United States Patent
Kuroiwa et al.

(10) Patent No.: US 11,344,535 B2
(45) Date of Patent: May 31, 2022

(54) PHARMACEUTICAL COMPOSITION

(71) Applicant: KOWA COMPANY, LTD., Nagoya (JP)

(72) Inventors: Yuki Kuroiwa, Fuji (JP); Akito Minamizono, Fuji (JP)

(73) Assignee: KOWA COMPANY, LTD., Nagoya (JP)

( * ) Notice: Subject to any disclaimer, the term of this patent is extended or adjusted under 35 U.S.C. 154(b) by 0 days.

(21) Appl. No.: 16/627,061

(22) PCT Filed: Jun. 29, 2018

(86) PCT No.: PCT/JP2018/024882
§ 371 (c)(1),
(2) Date: Dec. 27, 2019

(87) PCT Pub. No.: WO2019/004447
PCT Pub. Date: Jan. 3, 2019

(65) Prior Publication Data
US 2020/0222370 A1 Jul. 16, 2020

(30) Foreign Application Priority Data
Jun. 30, 2017 (JP) .............................. JP2017-128406

(51) Int. Cl.
A61K 31/423 (2006.01)
A61K 9/14 (2006.01)
A61K 9/20 (2006.01)
A61K 9/48 (2006.01)

(52) U.S. Cl.
CPC .............. A61K 31/423 (2013.01); A61K 9/14 (2013.01); A61K 9/20 (2013.01); A61K 9/48 (2013.01)

(58) Field of Classification Search
CPC .................................. A61K 31/423; A61K 9/14
See application file for complete search history.

(56) References Cited

U.S. PATENT DOCUMENTS

| 2003/0224058 A1 | 12/2003 | Ryde et al. |
| 2005/0101636 A1 | 5/2005 | Yamazaki et al. |
| 2015/0196538 A1 | 7/2015 | Takizawa et al. |
| 2016/0136138 A1 | 5/2016 | Shibata et al. |

FOREIGN PATENT DOCUMENTS

| JP | 2010-13462 A | 1/2010 |
| WO | WO 2005/023777 A1 | 3/2005 |
| WO | WO 2014/050134 A1 | 4/2014 |
| WO | WO 2014/051024 A1 | 4/2014 |
| WO | WO 2015/005365 A1 | 1/2015 |
| WO | WO 2016/084950 A1 | 6/2016 |
| WO | WO 2017/082377 A1 | 5/2017 |

OTHER PUBLICATIONS

International Search Report dated Aug. 21, 2018 in PCT/JP2018/024882 filed on Jun. 29, 2018, 2 pages.

Fruchart, J-C., "Selective peroxisome proliferator-activated receptorα modulators (SPPARMα): The next generation of peroxisome proliferator-activated receptor α-agonists," Cardiovascular Diabetology, vol. 12, No. 82, 2013, pp. 1-8.

Hennuyer N. et al., "The novel selective PPARα modulator (SPPARMα) pemafibrate improves dyslipidemia, enhances reverse cholesterol transport and decreases inflammation and atherosclerosis," Atherosclerosis, vol. 249, 2016, pp. 200-208.

"Report on the deliberation results of parmodia tablets 0.1 mg," Pharmaceutical Evaluation Division of Pharmaceutical Safety and Environmental Health Bureau, Ministry of Health, Labour and Welfare, Jul. 3, 2017, 83 total pages (with partial English translation).

Yamazaki, Y. et al., "Enantioselective Synthesis of the PPARα Agonist (R)-K-13675 via (S)-2-Hydroxybutyrolactone," Synthesis, 2008, No. 7, pp. 1017-1022, 7 total pages.

Notice of Reasons for Refusal dated Mar. 30, 2021 in Japanese Patent Application No. 2019-527070 (with English machine translation), 6 pages.

Naoki Wakiyama, "Stability and Shelf Life of Pharmaceuticals," Materials Life, vol. 3, No. 2, Apr. 1991, 13 pages (with partial English machine translation).

Primary Examiner — Kamal A Saeed

(74) Attorney, Agent, or Firm — Oblon, McClelland, Maier & Neustadt, L.L.P.

(57) ABSTRACT

Provided is a pharmaceutical composition containing pemafibrate, a salt thereof or a solvate thereof and having excellent storage stability. The pharmaceutical composition is provided to contain pemafibrate, a salt thereof or a solvate thereof, wherein a pH value of a solution produced by dissolving or dispersing the pharmaceutical composition in water is 7 or more.

10 Claims, No Drawings

PHARMACEUTICAL COMPOSITION

FIELD OF THE INVENTION

The present invention relates to a pharmaceutical composition etc.

BACKGROUND OF THE INVENTION

It is known that pemafibrate (Chemical Name: (2R)-2-[3-([1,3-Benzoxazol-2-yl[3-(4-methoxyphenoxy)propyl]amino]methyl)phenoxy]butanoic acid) (International Nonproprietary Name: pemafibrate) represented by the following structural formula:

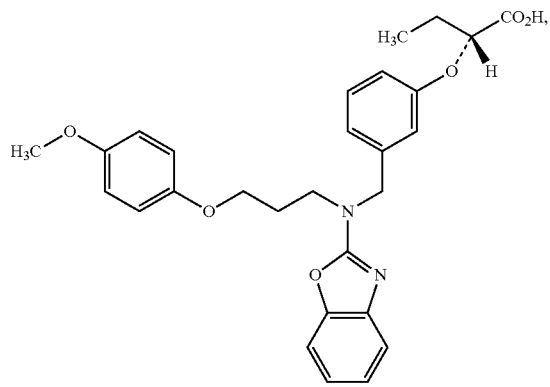

a salt thereof or a solvate thereof has excellent PPAR-α agonist activity, exhibits plasma triglyceride concentration reducing action, HDL cholesterol increasing action, etc., and is useful for prevention and treatment of dyslipidemia (hyperlipidemia) (Patent Document 1 and Non-Patent Documents 1 and 2), and useful for prevention and treatment of NAFLD (non-alcoholic fatty liver disease) (Patent Document 2).

Meanwhile, a compound useful as an active component for a pharmaceutical preparation is normally formulated as some pharmaceutical composition, and administered, and it is not unusual that a long time passes until a pharmaceutical composition is administered after production of the pharmaceutical composition. Thus, from the viewpoint of exhibiting expected drug efficacy and avoiding unanticipated adverse side effects, it is very important to secure stability of active components in the pharmaceutical composition.

PRIOR ART DOCUMENTS

Patent Documents

Patent Document 1: International Publication No. WO 2005/023777
Patent Document 2: International Publication No. WO 2015/005365

Non-Patent Documents

Non-Patent Document 1: Yukiyoshi Yamazaki, et al., Synthesis, 2008(7), 1017-1022.

Non-Patent Document 2: Fruchart J C., Cardiovasc Diabetol., 2013; 12: 82.

SUMMARY OF THE INVENTION

Problems to be Solved by the Invention

However, stability of active components significantly depends on the physical and chemical properties of components, but it is often impossible to predict such properties from the chemical structures or the like of the components, and there are not a few cases where a problem becomes evident only when a pharmaceutical composition is actually produced. Thus, establishment of a technique for securing stability of active components in a pharmaceutical composition commonly requires considerable try and error.

Pemafibrate, a salt thereof or a solvate thereof has been only reported to exhibit the above-described pharmacological effects, and has heretofore not been specifically studied in terms of a pharmaceutical composition, and stability in a pharmaceutical composition has heretofore not been reported at all.

In these circumstances, for providing a pharmaceutical composition containing pemafibrate and having excellent stability, the present inventors have extensively conducted studies on the physical and chemical properties of pemafibrate, and found that pemafibrate is extremely unstable under a low pH environment so as to produce decomposition products, though pemafibrate itself is mild acidic and has a low pH.

Thus, an object of the present invention is to provide a pharmaceutical composition which contains pemafibrate, a salt thereof or a solvate thereof and has excellent stability.

Means for Solving the Problems

In view of the above, the present inventors have further extensively conducted studies of stability of pemafibrate, and found that pemafibrate is extremely stabile in a high pH environment and that a pharmaceutical composition containing pemafibrate and having good stability can be obtained when formulated so that a pH value of a solution produced by dissolving or dispersing the pharmaceutical composition in water is 7 or more. The present invention has been accomplished on the basis of this finding.

Accordingly, the present invention provides a pharmaceutical composition comprising pemafibrate, a salt thereof or a solvate thereof, wherein a pH value of a solution produced by dissolving or dispersing the pharmaceutical composition in water is 7 or more.

The present invention also provides a method for stabilizing pemafibrate, a salt thereof or a solvate thereof in a pharmaceutical composition, the method comprising the step of formulating a pharmaceutical composition comprising pemafibrate, a salt thereof or a solvate thereof so that a pH value of a solution produced by dissolving or dispersing the pharmaceutical composition in water is 7 or more.

Effects of the Invention

According to the present invention, it is possible to provide a pharmaceutical composition containing pemafibrate, a salt thereof or a solvate thereof and having good stability.

DETAILED DESCRIPTION OF THE INVENTION

<Pemafibrate, Salt Thereof or Solvate Thereof>

Herein, "pemafibrate, a salt thereof or a solvate thereof" includes pemafibrate (Chemical Name: (2R)-2-[3-([1,3-Benzoxazol-2-yl[3-(4-methoxyphenoxy)propyl]aminolmethyl)phenoxy]butanoic acid) (International Nonproprietary Name: pemafibrate) itself, a pharmaceutically acceptable salt of pemafibrate and a solvate of pemafibrate or a pharmaceutically acceptable salt thereof with water, alcohol (for example ethanol) or the like. The pharmaceutically acceptable salt is not particularly limited, and examples thereof include acid addition salts and base addition salts. Specific examples of the acid addition salts include acid addition salts with inorganic acids, such as hydrochlorides, hydrobromides, hydroiodides, sulfate salts, nitrate salts and phosphate salts; and acid addition salts with organic acids, such as benzoate salts, methanesulfonate salts, ethanesulfonate salts, benzenesulfonate salts, p-toluenesulfonate salts, maleate salts, fumarate salts, tartrate salts, citrate salts and acetate salts. Specific examples of the base addition salts include metal salts such as sodium salts, potassium salts, lithium salts, calcium salts and magnesium salts; salts with amines such as ammonia, trimethylamine, triethylamine, pyridine, collidine and lutidine; and base addition salts with organic bases such as lysine, arginine, cinchonine and cinchonidine.

Pemafibrate, a salt thereof or a solvate thereof is a known compound, and can be produced through a method as disclosed in Patent Document 1, Non-Patent Document 1 or U.S. Pat. No. 7,109,226, for example. In the present invention, a pemafibrate crystal which can be produced through the method described in Non-Patent Document 1 (preferably a crystal showing a melting point of 95 to 101° C., particularly preferably 97 to 100° C. in measurement performed in accordance with The Japanese Pharmacopoeia, 17th Edition, Melting Point Determination Method 1) is preferably used. The disclosures of the documents are incorporated herein by reference.

The content of pemafibrate, a salt thereof or a solvate thereof in the pharmaceutical composition is not particularly limited, and can be determined in appropriate consideration of the type of preparation, the sex, age and symptoms of a patient in need of the composition, and the like. For example, the content can be set so that the daily dose of pemafibrate, a salt thereof or a solvate thereof may be 0.05 to 0.8 mg, more preferably 0.075 to 0.6 mg, particularly preferably 0.1 to 0.4 mg, in terms of a free form of pemafibrate.

The content of pemafibrate, a salt thereof or a solvate thereof in the pharmaceutical composition is preferably 0.01 to 5 mass %, more preferably 0.01 to 1 mass %, particularly preferably 0.05 to 0.5 mass %, in terms of a free form of pemafibrate, with respect to the total mass of the pharmaceutical composition.

Herein, the "a pH value of a solution produced by dissolving or dispersing a pharmaceutical composition in water" means a value obtained by measuring at 25° C. a pH of a solution produced by dissolving or dispersing a pharmaceutical composition containing pemafibrate, a salt thereof or a solvate thereof in water so that the concentration of pemafibrate in terms of a free form is 5 µg/mL. Incidentally, purified water is used as water.

A pH value of a solution produced by dissolving or dispersing a pharmaceutical composition in water is required to be 7 or more from the viewpoint of stability of pemafibrate, preferably about 7.0 or more (more preferably from about 7.0 to about 12.0), more preferably about 8.0 or more (more preferably from about 8.0 to about 12.0), still more preferably higher than about 8.0 (more preferably from higher than about 8.0 to about 12.0 or less), particularly preferably about 9.0 or more (more preferably from about 9.0 to about 12.0). Herein, the expression "7 or more" conceptually includes all over the range whose rounded result from one decimal place is 7.

The specific means for adjusting the pH value of the solution obtained by dissolving or dispersing the pharmaceutical composition in water to the above range is not particularly limited, and a person skilled in the art can appropriately adjust the pH value by adjusting the type and amount of components such as additives for pharmaceutical preparation while suitably checking the pH value. Specifically, a means for blending a neutral to basic pharmaceutically acceptable carrier (additives for pharmaceutical preparation) (e.g., those having a pH value within the above-mentioned range when dissolved or dispersed in water at 25° C.) with the pharmaceutical composition can be used, for example.

The neutral to basic additives for pharmaceutical preparation are not particularly limited, and examples thereof include: cellulose species such as celluloses or salts thereof (e.g., crystalline cellulose, powdered cellulose, etc.), hydroxyalkylcelluloses or salts thereof (e.g., hydroxyethylcellulose, hypromellose, hydroxypropylcellulose (incidentally, hydroxypropylcellulose may be either low substituted hydroxypropylcellulose or non-low substituted hydroxypropylcellulose), methylcellulose, etc.) and carboxyalkylcelluloses or derivatives (cross-linked polymers) thereof or salts thereof (e.g., carmellose sodium, croscarmellose sodium, etc.); starch species such as rice starch, α-cyclodextrin, β-cyclodextrin, potato starch, sodium carboxymethyl starch and hydroxypropyl starch; crospovidone; antacids such as magnesium aluminosilicate, calcium silicate, magnesium silicate, aluminum magnesium silicate, synthetic aluminum silicate, synthetic hydrotalcite, magnesium oxide, magnesium hydroxide-aluminum hydroxide co-precipitate, aluminum hydroxide gel, dried aluminum hydroxide gel, aluminum hydroxide gel-sodium hydrogen carbonate coprecipitation product, magnesium carbonate-calcium carbonate coprecipitation product, magnesium hydroxide, magnesium hydroxide-potassium aluminum sulfate coprecipitation product, sodium hydrogen carbonate, magnesium carbonate, magnesium carbonate mixture dry gel, calcium carbonate, precipitated calcium carbonate, disodium hydrogen phosphate anhydrous, meglumine, magnesium aluminometasilicate, dibasic potassium phosphate, dibasic calcium phosphate, anhydrous dibasic calcium phosphate, kaolin and bentonite; polyhydric alcohols such as polyvinyl alcohol (of fully saponified type), polyvinyl alcohol (of partially saponified type), macrogol 4000 and macrogol 6000; basic amino acids such as L-arginine and L-histidine; carboxylate salts such as sodium L-ascorbate, sodium L-aspartate, sodium alginate, calcium disodium edetate, tetrasodium edetate, tetrasodium edetate tetrahydrate salt, xanthan gum, sodium citrate hydrate, trisodium glycyrrhizate, calcium gluconate hydrate, monosodium L-glutamate, sodium succinate hexahydrate, sodium salicylate, sodium L-tartrate, potassium sodium tartrate, calcium pantothenate, and partially neutralized polyacrylic acid and anhydrous sodium citrate; phosphate salts such as disodium 5'-inosinate, disodium 5'-guanylate and anhydrous sodium pyrophosphate; sulfate salts such as dry sodium sulfite and sodium chondroitin sulfate; polysaccharides such as guar gum; polyoxyethylene hydrogenated castor oil such as polyoxyethylene hydrogenated castor oil 40 and polyoxyethylene hydrogenated castor oil 50; and acesulfame potassium. These may be used singly, or in combinations of two or more thereof.

Each of these neutral to basic additives for pharmaceutical preparation is a known component. These additives may be produced through a known method, or commercially available products may be used. Examples of the commercially available products include sodium ascorbate (BASF Japan Ltd.), sodium L-aspartate (Showa Kako Corporation), L-arginine (AJINOMOTO CO.,INC), Keltone (ISP Japan, Ltd.), disodium 5'-inosinate (AJINOMOTO CO., INC), calcium disodium edetate (DAIICHI PURE CHEMICALS CO., LTD.), anhydrous sodium sulfite (Nissan Chemical Corporation), xanthan gum (San-Ei Gen F.F.I., Inc.), disodium 5'-guanylate (AJINOMOTO CO., INC), ECG-505 (San-Ei Gen F.F.I., Inc.), sodium citrate hydrate (San-Ei Gen F.F.I., Inc.), calcium gluconate (Tomita Pharmaceutical Co., Ltd.), monosodium L-glutamate (AJINOMOTO CO.,INC), Ac-Di-Sol (Asahi Kasei Corporation), Kollidon CL (BASF Japan Ltd.), Neusilin A (Fuji Chemical Industries Co., Ltd.), FLORITE (Tokuyama Corporation), Magnesium Silicate (Tomita Pharmaceutical Co., Ltd.), magnesium aluminum silicate (Tomita Pharmaceutical Co., Ltd.), CEOLUS (San-Ei Gen F.F.I., Inc.), synthetic aluminum silicate (Tomita Pharmaceutical Co., Ltd.), Synthetic Hydrotalcite (Tomita Pharmaceutical Co., Ltd.), sodium succinate hexahydrate (UENO FINE CHEMICALS INDUSTRY, LTD.), sodium chondroitin sulfate (Nichi-Iko Pharmaceutical Co., Ltd.), magnesium oxide (San-Ei Gen F.F.I., Inc.), sodium L-tartrate (Showa Kako Corporation), potassium sodium tartrate (Showa Kako Corporation), SANALMIN (Kyowa Chemical Industry Co., Ltd.), aluminum hydroxide (SHOWA DENKO K.K.), aluminum hydroxide gel (Tomita Pharmaceutical Co., Ltd.), Kumulite (Kyowa Chemical Industry Co., Ltd.), SANALMIN B (Kyowa Chemical Industry Co., Ltd.), CAVAMAX W6 Pharma (CycloChem Co., Ltd.), CAVAMAX W7 Pharma (CycloChem Co., Ltd.), magnesium hydroxide (Tomita Pharmaceutical Co., Ltd.), calcium carbonate (Kishida Chemical Co., Ltd.), magnesium carbonate (Tomita Pharmaceutical Co., Ltd.), precipitated calcium carbonate (JUNSEI CHEMICAL CO., LTD.), L-HPC (Shin-Etsu Chemical Co., Ltd.), Potato Starch (Matsutani Chemical Industry Co., Ltd.), calcium pantothenate (San-Ei Gen F.F.I., Inc.), Nartrosol (ISP Japan, Ltd.), HPS-101 (Freund Corporation), hydroxypropylcellulose (Nippon Soda Co., Ltd.), AQUPAANA (SUMITOMO SEIKA CHEMICALS), KURARAY POVAL (KURARAY CO., LTD.), TC-5 (Shin-Etsu Chemical Co., Ltd.), ARBOCEL (Rettenmaier Japan Co., Ltd.), NIKKOL HCO-40 (Nikko Chemicals Co., Ltd.), NIKKOL HCO-50 (Nikko Chemicals Co., Ltd.), Gohsenol (Nippon Synthetic Chemical Industry Co., Ltd.), Macrogol 200 (NOF CORPORATION), Macrogol 4000 (NOF CORPORATION), Macrogol 6000 (NOF CORPORATION), Macrogol 20000 (NOF CORPORATION), anhydrous sodium citrate (Showa Kako Corporation), disodium hydrogen phosphate anhydrous (Wako Pure Chemical Industries, Ltd.), Neusilin (Fuji Chemical Industries Co., Ltd.), METOLOSE (Shin-Etsu Chemical Co., Ltd.) and dibasic potassium phosphate (San-Ei Gen F.F.I., Inc.).

The pharmaceutical composition of the present invention is preferably one adjusted to have the above-mentioned range of pH value by using one or more selected from the group consisting of cellulose species, starch species, crospovidone, antacids and carboxylate salts, more preferably one adjusted to have the above-mentioned range of pH value by using one or more one selected from the group consisting of cellulose species, starch species and crospovidone.

Herein, the dosage form of the "pharmaceutical composition" is not particularly limited, may be a solid, semisolid or liquid preparation, and can be selected according to the use purpose of the pharmaceutical composition. Examples of the dosage form of the pharmaceutical composition include dosage forms described in The Japanese Pharmacopoeia, 17th Edition, General Rules for Preparations. Specific examples of the peroral dosage form include solid preparations such as tablets (e.g. normal tablets, orally disintegrating tablets, chewable tablets, effervescent tablets, dispersion tablets and soluble tablets), capsules, granules (e.g. effervescent granules), powders and pills; semisolid preparations such as peroral jellies; liquid preparations such as peroral liquids (e.g. elixirs, suspensions, emulsions and lemonades). Examples of the parenteral dosage form include injections, inhalations, eye drops, ear drops, nasal drops, suppositories, solid external preparations, liquid external preparations, sprays, ointments, creams, gels and patches.

From the viewpoint of ease of administration and ease of production, the dosage form of the pharmaceutical composition is preferably a solid preparation, particularly preferably a solid preparation selected from the group consisting of a tablet (e.g. normal tablet, orally disintegrating tablet, chewable tablet, effervescent tablet, dispersion tablet or soluble tablet), a capsule, a granule (e.g. effervescent granule), a powder and a pill.

The pharmaceutical composition of the present invention can be produced through a known method depending on its dosage form.

For example, the pharmaceutical composition, when it is a solid preparation, can be produced through appropriate combination of unit operations such as grinding, mixing, granulation, drying, grain size adjustment, classification, filling, pelletizing and coating.

More specifically, for example, when the dosage form of the pharmaceutical composition is a granular preparation such as a granule, a powder or a pill, additives for pharmaceutical preparation such as diluents, binders, disintegrants and lubricants are used, and after mixing these components in accordance with needs, the mixture is granulated through a known granulation method such as extrusion granulation, tumbling granulation, agitation granulation, fluidized bed granulation, spray granulation, melt granulation or crushing granulation to obtain a granulated product, and the granulated product is subjected to classification, grain size adjustment and the like in accordance with needs, whereby the pharmaceutical composition can be produced. The obtained granulated product can be coated through a known method with a coating agent etc.

When the dosage form of the pharmaceutical composition is a tablet, appropriate additives for pharmaceutical preparation such as diluents, binders, disintegrants and lubricants are used in accordance with needs, and these components are mixed to obtain the mixture, which is then directly compressed (pelletized) (through a direct powder compression method), or compressed (pelletized) (through a semidry grain compression method, dry granule compression method, wet grain compression method or the like) after the aforementioned granulated product is subjected to classification, grain size adjustment and the like, whereby the pharmaceutical composition can be produced. The obtained compressed product (tablet) can be coated through a known method with a coating agent etc.

When the dosage form of the pharmaceutical composition is a capsule, the granulated product or compressed product may be capsulated.

Pharmaceutically acceptable carriers (additives for pharmaceutical preparation) may be added to the pharmaceutical composition depending on its dosage form. Examples of the additives for pharmaceutical preparation include, but are not limited to, diluents, disintegrants, binders, lubricants, plasticizers, film formers, powders, poorly water-soluble polymer substances, antioxidants, flavors and sweetening agents. As specific examples of these additives for pharmaceutical preparation, those described in Japanese Pharmaceutical Excipients Directory 2016 (issued by Yakuji Nippo, Limited), Handbook of Pharmaceutical Excipients, Seventh Edition (issued by Pharmaceutical Press), etc. may be used. Furthermore, the above-mentioned neutral to basic additives for pharmaceutical preparation may be used as the additives for pharmaceutical preparation.

Specific examples of the diluents include: inorganic diluents such as aluminum silicate, anhydrous sodium sulfate, sodium chloride, light anhydrous silicic acid, heavy anhydrous silicic acid, calcium sulfate, calcium monohydrogen phosphate, dibasic sodium phosphate, monobasic potassium phosphate, monobasic calcium phosphate and sodium dihydrogen phosphate; and organic diluents such as corn syrup solids, starch (wheat starch, rice starch, corn starch, partially pregelatinized starch, etc.), fructose, caramel, agar, xylitol, paraffin, crystalline cellulose, powdered cellulose, sucrose, maltose, lactose, lactose monohydrate, white soft sugar, glucose, pullulan, polyoxyethylene hydrogenated castor oil, maltitol, reduced maltose starch syrup, powdery reduced maltose starch syrup, erythritol, sorbitol, mannitol, lactitol, trehalose, reduced palatinose, aminoalkyl methacrylate copolymer E, polyvinylacetal diethylaminoacetate and calcium citrate. These diluents may be used singly, or in combinations of two or more thereof.

Among these diluents, light anhydrous silicic acid, crystalline cellulose, lactose monohydrate, white soft sugar and mannitol are preferable.

Specific examples of the disintegrants include superdisintegrants such as carboxymethyl starch sodium, croscarmellose sodium and crospovidone, carmellose, carmellose calcium, starch, sucrose fatty acid ester, gelatin, dextrin, dehydroacetic acid and salts thereof, povidone and polyoxyethylene hydrogenated castor oil 60. These disintegrants may be used singly, or in combinations of two or more thereof.

Among these disintegrants, carboxymethyl starch sodium and croscarmellose sodium are preferable.

Specific examples of the binders include oils and fats such as tallow hydrogenated oil, hydrogenated oil, hydrogenated vegetable oil, soybean hydrogenated oil, carnauba wax, white beeswax, yellow beeswax and Japan wax, methylcellulose, hydroxypropylcellulose, hypromellose, carmellose sodium, starch (wheat starch, rice starch, corn starch, partially pregelatinized starch, etc.), dextrin, pullulan, acacia, agar, gelatin, tragacanth, sodium alginate, povidone, polyvinyl alcohol, aminoalkyl methacrylate copolymer E and polyvinylacetal diethylaminoacetate. These binders may be used singly, or in combinations of two or more thereof.

Among these binders, carnauba wax, hydroxypropylcellulose, hypromellose, povidone and aminoalkyl methacrylate copolymer E are preferable.

Specific examples of the lubricants include calcium stearate, magnesium stearate, sodium stearyl fumarate and sucrose fatty acid ester. Theses lubricants may be used singly, or in combinations of two or more thereof.

Among these lubricants, calcium stearate, magnesium stearate and sodium stearyl fumarate are preferable.

Specific examples of the plasticizers include triethyl citrate, glycerin, sesame oil, sorbitol, castor oil and polysorbate 80 (polyoxyethylene(20) sorbitan oleate). These plasticizers may be used singly, or in combinations of two or more thereof.

Among these plasticizers, triethyl citrate, glycerin and sorbitol are preferable.

Specific examples of the film formers include alkylcelluloses such as methylcellulose and ethylcellulose; alginic acid or salts thereof such as sodium alginate; carrageenan; carboxyalkylcelluloses such as carboxymethylcellulose sodium, carboxymethylcellulose calcium, carboxymethylcellulose potassium, carboxymethylcellulose and carboxymethylethylcellulose; xanthan gum; hydroxyalkylcelluloses such as hydroxymethylcellulose, hydroxyethylcellulose, hydroxypropylcellulose, hypromellose (hydroxypropylmethylcellulose); hydroxyalkylcellulose phthalate such as hydroxypropylmethylcellulose phthalate; pullulan; polyvinyl acetate; polyvinyl acetate phthalate; and polyvinylpyrrolidone. These film formers may be used singly, or in combinations of two or more thereof.

Among these film formers, alkylcelluloses and hydroxyalkylcelluloses are preferable.

Specific examples of the powders include organic and inorganic powders such as powders of talc, titanium oxide, yellow ferric oxide, red ferric oxide and legal color pigments. These powders may be used singly, or in combinations of two or more thereof.

Among these powders, titanium oxide, yellow ferric oxide, red ferric oxide and legal color pigments are preferable.

Specific examples of the poorly water-soluble polymer substances include carboxyvinyl polymers and aminoalkyl methacrylate copolymers. These substances may be used singly, or in combinations of two or more thereof.

Specific examples of the antioxidants include ascorbic acid, sodium hydrogen sulfite, sodium sulfite, sodium edetate, erythorbic acid, tocopherol acetate, dibutylhydroxytoluene, natural vitamin E, tocopherol and butylhydroxyanisole. These antioxidants may be used singly, or in combinations of two or more thereof.

Specific examples of the flavors include terpenes such as limonene, pinene, camphene, cymene, cineole, citronellol, geraniol, nerol, linalool, menthol, terpineol, rhodinol, borneol, isoborneol, menthone, camphor, eugenol and cinnzeylanol; terpene-containing essential oils such as bitter orange oil, orange oil, peppermint oil, camphor white oil, eucalyptus oil, turpentine oil, lemon oil, ginger oil, clove oil, cinnamon oil, lavender oil, fennel oil, chamomile oil, fermented soybean oil and spearmint oil; and acidifiers such as ascorbic acid, tartaric acid, citric acid, malic acid and salts thereof. These flavors may be used singly, or in combinations of two or more thereof.

Examples of the sweetening agents include aspartame, stevia, sucralose, glycyrrhizic acid, thaumatin, acesulfame potassium, saccharin and saccharin sodium, and these sweetening agents may be used singly, or in combinations of two or more thereof.

The pharmaceutical composition of the present invention preferably contains one or more selected from the group consisting of lactose monohydrate, croscarmellose sodium, hydroxypropylcellulose, crystalline cellulose, magnesium stearate, titanium oxide, triethyl citrate, hypromellose, light anhydrous silicic acid and carnauba wax, among the above-mentioned pharmaceutically acceptable carriers.

The disease to which the pharmaceutical composition of the present invention is applied is not limited, and the pharmaceutical composition can be widely used for prevention or treatment of diseases against which administration of pemafibrate is known or expected to be effective.

For example, pemafibrate, a salt thereof or a solvate thereof has excellent PPAR-α agonist activity, and exhibits plasma triglyceride concentration reducing action, HDL cholesterol increasing action, etc. Therefore, the pharmaceutical composition of the present invention can be used preferably as an agent for prevention and/or treatment of dyslipidemia (hyperlipidemia, more specifically, for example primary hyperlipidemia and secondary hyperlipidemia), further preferably as an agent for prevention and/or treatment of hypertriglyceridemia, etc.

In addition, pemafibrate, a salt thereof or a solvate thereof is useful for prevention or treatment of NAFLD (non-alcoholic fatty liver disease). Therefore, the pharmaceutical composition of the present invention can also be used as an agent for prevention and/or treatment of NAFLD (more preferably NASH (non-alcoholic steatohepatitis)), etc.

Further, pemafibrate, a salt thereof or a solvate thereof may be used as an agent for treatment of primary biliary cirrhosis, etc.

The administration route of the pharmaceutical composition is not particularly limited, and can be determined in appropriate consideration of the target disease, the type of preparation, the sex, age, symptoms of a patient in need of the composition, and the like, but peroral administration is preferable from the viewpoint of ease of administration. The daily dose of the pharmaceutical composition can be taken as a single dose, or can be divided into 2 to 4 daily administrations, and taken before each meal, between meals, after each meal, before bedtime, or the like.

For example, the following aspects are disclosed herein and should not be construed as limiting the present invention.

[1-1] A pharmaceutical composition comprising pemafibrate, a salt thereof or a solvate thereof, wherein a pH value of a solution produced by dissolving or dispersing the pharmaceutical composition in water is 7 or more (preferably about 7.0 or more (more preferably from about 7.0 to about 12.0), more preferably about 8.0 or more (more preferably from about 8.0 to about 12.0), still more preferably higher than about 8.0 (more preferably from higher than about 8.0 to about 12.0 or less), particularly preferably about 9.0 or more (more preferably from about 9.0 to about 12.0)).

[1-2] A pharmaceutical composition comprising pemafibrate, a salt thereof or a solvate thereof and a pharmaceutically acceptable carrier, wherein a pH value of a solution produced by dissolving or dispersing the pharmaceutical composition in water is 7 or more (preferably about 7.0 or more (more preferably from about 7.0 to about 12.0), more preferably about 8.0 or more (more preferably from about 8.0 to about 12.0), still more preferably higher than about 8.0 (more preferably from higher than about 8.0 to about 12.0 or less), particularly preferably about 9.0 or more (more preferably from about 9.0 to about 12.0)).

[1-3] The pharmaceutical composition according to [1-2], wherein one or more selected from the group consisting of cellulose species, starch species, crospovidone, antacids and carboxylate salts is used as the pharmaceutically acceptable carrier, and a pH value of a solution produced by dissolving or dispersing the pharmaceutical composition in water is 7 or more (preferably about 7.0 or more (more preferably from about 7.0 to about 12.0), more preferably about 8.0 or more (more preferably from about 8.0 to about 12.0), still more preferably higher than about 8.0 (more preferably from higher than about 8.0 to about 12.0 or less), particularly preferably about 9.0 or more (more preferably from about 9.0 to about 12.0)).

[1-4] The pharmaceutical composition according to any one of [1-1] to [1-3], comprising one or more selected from the group consisting of lactose monohydrate, croscarmellose sodium, hydroxypropylcellulose, crystalline cellulose, magnesium stearate, titanium oxide, triethyl citrate, hypromellose, light anhydrous silicic acid and carnauba wax.

[1-5] The pharmaceutical composition according to any one of [1-1] to [1-4], wherein the pharmaceutical composition is a solid preparation.

[1-6] The pharmaceutical composition according to any one of [1-1] to [1-5], wherein a dosage form thereof is a tablet, a capsule, a granule, a powder or a pill.

[1-7] The pharmaceutical composition according to any one of [1-1] to [1-6], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

For example, the following aspects are disclosed herein and should not be construed as limiting the present invention.

[2-1] A method for stabilizing pemafibrate, a salt thereof or a solvate thereof in a pharmaceutical composition, the method comprising the step of formulating a pharmaceutical composition comprising pemafibrate, a salt thereof or a solvate thereof so that a pH value of a solution produced by dissolving or dispersing the pharmaceutical composition in water is 7 or more (preferably about 7.0 or more (more preferably from about 7.0 to about 12.0), more preferably about 8.0 or more (more preferably from about 8.0 to about 12.0), still more preferably higher than about 8.0 (more preferably from higher than about 8.0 to about 12.0 or less), particularly preferably about 9.0 or more (more preferably from about 9.0 to about 12.0)).

[2-2] A method for stabilizing pemafibrate, a salt thereof or a solvate thereof in a pharmaceutical composition, the method comprising the step of formulating a pharmaceutical composition comprising pemafibrate, a salt thereof or a solvate thereof and a pharmaceutically acceptable carrier so that a pH value of a solution produced by dissolving or dispersing the pharmaceutical composition in water is 7 or more (preferably about 7.0 or more (more preferably from about 7.0 to about 12.0), more preferably about 8.0 or more (more preferably from about 8.0 to about 12.0), still more preferably higher than about 8.0 (more preferably from higher than about 8.0 to about 12.0 or less), particularly preferably about 9.0 or more (more preferably from about 9.0 to about 12.0)).

[2-3] The method according to [2-2], wherein the formulating step is performed using one or more selected from the group consisting of cellulose species, starch species, crospovidone, antacids and carboxylate salts as the pharmaceutically acceptable carrier so that a pH value of a solution produced by dissolving or dispersing the pharmaceutical composition in water is 7 or more (preferably about 7.0 or more (more preferably from about 7.0 to about 12.0), more preferably about 8.0 or more (more preferably from about 8.0 to about 12.0), still more preferably higher than about 8.0 (more preferably from higher than about 8.0 to about 12.0 or less), particularly preferably about 9.0 or more (more preferably from about 9.0 to about 12.0)).

[2-4] The method according to any one of [2-1] to [2-3], wherein the pharmaceutical composition comprises one or more selected from the group consisting of lactose monohydrate, croscarmellose sodium, hydroxypropylcellulose, crystalline cellulose, magnesium stearate, titanium oxide, triethyl citrate, hypromellose, light anhydrous silicic acid and carnauba wax.

[2-5] The method according to any one of [2-1] to [2-4], wherein the pharmaceutical composition is a solid preparation.

[2-6] The method according to any one of [2-1] to [2-5], wherein a dosage form thereof is a tablet, a capsule, a granule, a powder or a pill.

[2-7] The method according to any one of [2-1] to [2-6], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

EXAMPLES

The present invention will next be described in detail by way of Examples, which should not be construed as limiting the invention thereto.

In Test Examples below, measurement was performed through HPLC using an ODS column as a column and an ultraviolet spectrophotometer as a detector.

Test Example 1

Studies of pH Value of Pemafibrate Itself, and Stability under Different pH Environments First a measurement of a pH value of pemafibrate itself was performed.

To be more specific, pemafibrate was dissolved or dispersed in purified water so that the concentration of pemafibrate as the free form was 5 μg/mL. Then, a pH value of the obtained solution at 25° C. was measured. The result is shown in Table 1.

Additionally, the following studies were conducted in order to evaluate the stability of pemafibrate under different pH environments.

Namely, buffer solutions were prepared in accordance with the descriptions about buffer solutions of U.S.Pharmacopeia (2013 Edition) and Japanese Pharmacopeia (17th Edition), so as to have the following pH values at 25° C.:

pH 2.0 (hydrochloric acid buffer solution including potassium chloride);
pH 3.0 and 4.0 (Acid phthalate buffer solution including potassium biphthalate);
pH 6.0 and 7.0 (phosphate buffer solution);
pH 8.0, 9.0 and 10.0 (Alkaline borate buffer solution including boric acid, potassium chloride and sodium hydroxide);
pH 11.0 (Ammonium buffer solution including ammonia and ammonium chloride); and
pH 12.0 (phosphate buffer solution).

In each of the buffer solutions, pemafibrate was dissolved or dispersed so that its amount as the free form was 5 μg/mL, thereby producing liquid samples having different pH conditions. The liquid samples were stored at 80° C. for 96 hours. The amounts of pemafibrate-derived decomposition products (related substances) in the liquid samples after storage for 96 hours were evaluated through the following method.

Specifically, acetonitrile was added to each of the liquid samples, and then they were measured by using HPLC. The sum of peak areas derived from related substances on the chromatogram was calculated in terms of the ratio (%) to the sum of peak areas derived from pemafibrate and related substances, and the ratio was defined as the "Total amount (%) of related substances".

Table 2 shows the results.

TABLE 1

| Pemafibrate concentration in aqueous solution/aqueous dispersion | pH value (25° C.) |
|---|---|
| 5 μg/mL | 5.9 |

TABLE 2

| | Total amount (%) of related substances | | | | | | | | | |
|---|---|---|---|---|---|---|---|---|---|---|
| pH value (25° C.) | 2.0 | 3.0 | 4.0 | 6.0 | 7.0 | 8.0 | 9.0 | 10.0 | 11.0 | 12.0 |
| 96 hours later | 27.1 | 4.1 | 1.1 | 1.3 | 0.9 | 0.4 | <0.1 | 0.1 | 0.1 | <0.1 |

The results shown in Table 1 reveal that pemafibrate itself is an acidic substance and has mild acidity (about pH 5.9) when it is dissolved or dispersed in water.

On the other hand, the results shown in Table 2 reveal that pemafibrate became remarkably unstable if the pH value was 6.0 or less and the amount of related substances was increased with the reduction of pH value, and meanwhile, pemafibrate is stable under environments having pH value of 7.0 or more, and particularly when pH value exceeded 8.0, the production of related substances could hardly be confirmed.

From the above test results, it was found that the stability of pemafibrate was not satisfactory under a pH environment of pemafibrate itself and that a pharmaceutical composition excellent in stability of pemafibrate could be obtained if the pH environment of pemafibrate is adjusted to a pH environment of 7 or more by any means such as the addition of pharmaceutical excipients.

Test Example 2

Stability Test

On the basis of the results of Test Example 1, a pharmaceutical composition (tablet) containing pemafibrate whose pH value as solution, produced by dissolving or dispersing a pharmaceutical composition in water, was adjusted to 7 or more by blending pharmaceutical excipients was produced and examined in terms of its stability.

Production of Tablets of Example 1

Pemafibrate, lactose monohydrate, croscarmellose sodium, hydroxypropylcellulose and microcrystalline cellulose were mixed together, then kneaded with purified water, granulated, dried, and then sized to obtain a granulated product. Magnesium stearate was mixed with the obtained granulated product, and the mixture was then compressed to obtain core tablets containing 0.1 mg of pemafibrate in terms of a free form of pemafibrate per tablet (120 mg).

Next, titanium oxide, triethyl citrate, hypromellose and light anhydrous silicic acid were dissolved/dispersed in purified water to obtain a film coating solution. The core tablet was coated with the film coating solution using a ventilation-type coater, and carnauba wax was added to polish the tablet glossy. Accordingly, film coating tablets each having a weight of 125 mg was obtained.

Examination of a pH Value of the Tablets of Example 1

The tablets of Example 1 were ground into a tablet-derived powder. The tablet-derived powder was dissolved/dispersed in purified water while adjusting the amount of purified water so that the concentration of pemafibrate in an aqueous solution or aqueous dispersion of the tablets is 5 μg/mL.
The thus obtained aqueous solution or aqueous dispersion of the tablets was subjected to a measurement in terms of a pH value, which resulted in 7.7.

Stability of Pemafibrate in the Tablets of Example 1

A polyethylene bottle was charged with the tablets of Example 1 and stored at 25° C. and 60% relative humidity for 24 months.
The amounts of pemafibrate-derived decomposition products (related substances) at the start of storage and after storage for 24 months were evaluated through the following method.
In other words, the tablets at the start of storage and after storage for 24 months were analyzed by using HPLC. The sum of peak areas derived from related substances on the chromatogram was calculated in terms of a ratio (%) to the sum of peak areas derived from pemafibrate and related substances, and the ratio was defined as the "Total amount (%) of related substances". Table 3 shows the results.

TABLE 3

|  | At the start of storage | After storage for 24 months |
|---|---|---|
| Total amount (%) of related substances | <0.05 | <0.05 |

As shown in Table 3, the tables of Example 1 (containing pemafibrate, a salt thereof or a solvate thereof, and its pH value as solution, produced by dissolving or dispersing a pharmaceutical composition in water, is 7.7) were excellent in stability, and there was actually no increase in the amount of related substances even after storage for 24 months.
From the above results, it was confirmed that if a pH environment of pemafibrate is brought to a high pH environment (7 or more) by the addition of pharmaceutical excipients, a pharmaceutical composition which is excellent in stability of pemafibrate can be obtained.

Production Examples 1 to 6

Tablets containing the components in the amounts (mg) thereof per tablet shown in Tables 4 and 5 are conventionally produced. The "pH value" in the tables means that of an aqueous solution or aqueous dispersion measured at 25° C., the aqueous solution or aqueous dispersion being prepared by grinding tablets of each Example into a tablet-derived powder and then dissolving/dispersing the powder in purified water having an amount so adjusted that the concentration of pemafibrate in water is 5 μg/mL.

TABLE 4

|  | Production Example 1 | Production Example 2 | Production Example 3 |
|---|---|---|---|
| Pemafibrate | 0.1 | 0.4 | 0.1 |
| Lactose monohydrate | q.s. | q.s. | q.s. |
| Magnesium stearate | 1.2 | 1.2 | 1.2 |
| Carmellose sodium | q.s. |  | 6 |
| Croscarmellose sodium | 1 |  |  |
| Crospovidone | 3 |  |  |
| Low-substituted hydroxypropylcellulose |  | 2 | 4 |
| Sodium carboxymethyl starch |  | 3 |  |
| Hydroxypropyl starch |  | 2 |  |
| Sodium alginate |  | q.s. | 0.5 |
| Hydroxyethylcellulose | 1 |  | 2 |
| Hydroxypropylcellulose | 1 |  |  |
| Hypromellose |  | 1 |  |
| Polyvinyl alcohol (Partially saponified type) |  |  | 1 |
| Methylcellulose | 1 |  |  |
| Magnesium L-aspartate |  |  | 1 |
| Aluminum hydroxide gel-sodium hydrogen carbonate coprecipitation product |  |  | 1 |
| Precipitated calcium carbonate |  |  | q.s. |
| Magnesium aluminosilicate |  |  | 3 |
| Aluminum magnesium silicate |  |  | 2 |
| Microcrystalline cellulose |  | 5 |  |
| α-cyclodextrin |  |  | 20 |
| Powdered cellulose | 50 |  |  |
| Magnesium hydroxide-aluminum hydroxide co-precipitate |  | 3 |  |
| Acesulfame potassium |  |  | 1 |
| Total | 100 mg | 100 mg | 100 mg |
| pH value | 6.8 | 7.3 | 7.5 |

TABLE 5

|  | Production Example 4 | Production Example 5 | Production Example 6 |
|---|---|---|---|
| Pemafibrate | 0.2 | 0.4 | 0.2 |
| Lactose monohydrate | q.s. | q.s. | q.s. |
| Magnesium stearate | 1.2 | 1.2 | 1.2 |
| Carmellose sodium |  |  | 1 |
| Croscarmellose sodium | 2 |  | 1 |
| Crospovidone | 20 |  |  |
| Sodium carboxymethyl starch |  | 1 |  |
| Potato starch |  | 15 |  |
| Hydroxypropyl starch |  |  | 3 |
| Hydroxypropylcellulose | 1 |  |  |
| Hypromellose |  | 0.5 |  |
| Polyvinyl alcohol (Fully saponified type) | 1 |  |  |
| Macrogol 4000 |  |  | 4 |
| Macrogol 6000 |  | 6 |  |
| Methylcellulose |  |  | 1 |
| Magnesium oxide | q.s. |  |  |
| Magnesium hydroxide |  | q.s. |  |
| Aluminium hydroxide gel | 1 |  |  |
| Dried aluminium hydroxide gel |  | 3 |  |
| Sodium hydrogen carbonate | 0.5 |  |  |
| Magnesium carbonate |  | 2 |  |
| Meglumine |  |  | q.s. |
| Magnesium aluminometasilicate |  | 1 |  |
| Sodium citrate hydrate |  |  | 3 |
| Calcium silicate | 1 |  |  |
| Magnesium silicate |  | 5 |  |
| Microcrystalline cellulose |  |  | 40 |
| Synthetic hydrotalcite |  | 6 |  |
| β-cyclodextrin | 40 |  |  |
| Dibasic calcium phosphate |  |  | 20 |
| Anhydrous dibasic calcium phosphate |  | 20 |  |
| Sodium L-ascorbate | 5 |  |  |

TABLE 5-continued

|  | Production Example 4 | Production Example 5 | Production Example 6 |
|---|---|---|---|
| Calcium chloride hydrate |  | 5 |  |
| Bentonite |  |  | 6 |
| Total | 100 mg | 100 mg | 100 mg |
| pH value | 7.9 | 8.2 | 9.5 |

INDUSTRIAL APPLICABILITY

The present invention enables provision of a pharmaceutical composition having excellent stability and containing pemafibrate which exhibits plasma triglyceride concentration reducing action, HDL cholesterol increasing action, etc. The pharmaceutical composition can be used in, for example, pharmaceutical preparation industries.

The invention claimed is:

1. A pharmaceutical composition comprising pemafibrate, a salt thereof or a solvate thereof, wherein a pH value of a solution produced by dissolving or dispersing the pharmaceutical composition in water is 7 or more.

2. The pharmaceutical composition according to claim 1, wherein the pH value is from 7.0 to 12.0.

3. The pharmaceutical composition according to claim 1, further comprising a neutral to basic pharmaceutically acceptable additive.

4. The pharmaceutical composition according to claim 1, wherein the pharmaceutical composition is a solid preparation.

5. The pharmaceutical composition according to claim 1, wherein a dosage form thereof is a tablet, a capsule, a granule, a powder or a pill.

6. A method for stabilizing pemafibrate, a salt thereof or a solvate thereof in a pharmaceutical composition, the method comprising the step of formulating a pharmaceutical composition comprising pemafibrate, a salt thereof or a solvate thereof so that a pH value of a solution produced by dissolving or dispersing the pharmaceutical composition in water is 7 or more.

7. The pharmaceutical composition of claim 1 wherein the pH value of a solution produced by dissolving or dispersing the pharmaceutical composition in water is higher than about 8 or more.

8. The pharmaceutical composition of claim 1 wherein the pH value of a solution produced by dissolving or dispersing the pharmaceutical composition in water is higher than about 8 to about 12.

9. The pharmaceutical composition of claim 1 wherein the pH value of a solution produced by dissolving or dispersing the pharmaceutical composition in water is higher than about 9 or more.

10. The pharmaceutical composition of claim 1 wherein the pH value of a solution produced by dissolving or dispersing the pharmaceutical composition in water is higher than about 9 to about 12.

* * * * *